(12) United States Patent
Schoenberg

(10) Patent No.: US 7,478,049 B2
(45) Date of Patent: Jan. 13, 2009

(54) TEXT GENERATION AND SEARCHING METHOD AND SYSTEM

(75) Inventor: Roy Schoenberg, Boston, MA (US)

(73) Assignee: CareKey, Inc., Boston, MA (US)

( * ) Notice: Subject to any disclaimer, the term of this patent is extended or adjusted under 35 U.S.C. 154(b) by 742 days.

(21) Appl. No.: 10/726,758

(22) Filed: Dec. 3, 2003

(65) Prior Publication Data

US 2005/0125435 A1 Jun. 9, 2005

(51) Int. Cl.
*G06F 19/00* (2006.01)
*G06F 17/30* (2006.01)

(52) U.S. Cl. ............ 705/3; 705/2; 707/3; 707/100

(58) Field of Classification Search ............ 707/2–5, 707/100; 705/1–3
See application file for complete search history.

(56) References Cited

U.S. PATENT DOCUMENTS

| | | | | |
|---|---|---|---|---|
| 4,882,474 A | | 11/1989 | Anderi et al. ............ 235/380 |
| 5,664,109 A | * | 9/1997 | Johnson et al. ............ 705/2 |
| 5,704,044 A | | 12/1997 | Tarter et al. ............ 395/204 |
| 5,781,897 A | * | 7/1998 | Chen et al. ............ 707/3 |
| 5,805,719 A | | 9/1998 | Pare, Jr. et al. ............ 382/115 |
| 5,895,462 A | * | 4/1999 | Toki ............ 707/3 |
| 6,076,166 A | | 6/2000 | Moshfeghi et al. ............ 713/201 |
| 6,256,640 B1 | * | 7/2001 | Smalley et al. ............ 707/104.1 |
| 6,308,171 B1 | * | 10/2001 | De La Huerga ............ 707/3 |
| 6,434,567 B1 | * | 8/2002 | De La Huerga ............ 707/102 |
| 6,463,417 B1 | | 10/2002 | Schoenberg ............ 705/2 |
| 6,516,321 B1 | * | 2/2003 | De La Huerga ............ 707/102 |
| 6,615,241 B1 | * | 9/2003 | Miller et al. ............ 709/206 |
| 6,912,549 B2 | * | 6/2005 | Rotter et al. ............ 707/200 |
| 7,013,289 B2 | * | 3/2006 | Horn et al. ............ 705/26 |
| 7,013,298 B1 | * | 3/2006 | De La Huerga ............ 707/3 |
| 2001/0049610 A1 | * | 12/2001 | Hazumi ............ 705/3 |
| 2002/0022973 A1 | * | 2/2002 | Sun et al. ............ 705/3 |
| 2003/0018638 A1 | * | 1/2003 | Abe et al. ............ 707/6 |
| 2004/0267703 A1 | * | 12/2004 | McEnery et al. ............ 707/3 |
| 2005/0060286 A1 | * | 3/2005 | Hansen et al. ............ 707/2 |
| 2005/0125446 A1 | * | 6/2005 | Schoenberg ............ 707/104.1 |
| 2007/0073559 A1 | * | 3/2007 | Stangel ............ 705/2 |

FOREIGN PATENT DOCUMENTS

WO WO01/26020 A1 4/2001

OTHER PUBLICATIONS

Annas, G., "A National Bill of Patient's Rights", NEJM, 338, p. 695-699, Mar. 5, 1998.
Bakker, A., "Security in Perspective; Luxury or Must?", Int. J. Med. Inf., 49, p. 31-37, 1998.

(Continued)

*Primary Examiner*—Cheryl Lewis
(74) *Attorney, Agent, or Firm*—Fulbright & Jaworski L.L.P.

(57) ABSTRACT

A text-generation method and system includes receiving data records, such that each data record includes one or more data fields and a field value associated with each data field. A text-string is generated for each data record, such that each text-string includes one or more text-based data descriptors. Each data descriptor includes a field descriptor that defines a specific data field within the data record to which the text-string is related, and a value descriptor that defines the field value associated with the specific data field.

46 Claims, 8 Drawing Sheets

OTHER PUBLICATIONS

Barrows, R. Jr. et al., "Privacy, Confidentiality, and Electronic Medical Records", J. Amer. Med. Inf. Assoc., 3, p. 139-148, Mar. 1996.

Cimino, J. et al., "Architecture for a Web-Based Clinical Information System that Keeps the Design Open and the Access Closed", Proc. AMIA Symp., p. 121-125, 1998.

Dudeck, J., "Aspects of Implementing and Harmonizing Healthcare Communication Standards", Int. J. Med. Inf., 48, p. 163-171, Feb. 1998.

Epstein, M. et al., "Security for the Digital Information Age of Medicine: Issues, Applications, and Implementation", J. Digit Imaging, 11, p. 33-44, Feb. 1998.

Espinosa, A., "Availability of Health Data: Requirements and Solutions", Int. J. Med. Inf., 49, p. 97-104, Mar. 1998.

Gibby, G. et al., "Availability of Records in An Outpatient Preanesthetic Evaluation Clinic", J. Clin. Mon. & Computing, 14, p. 385-391, Aug. 1998.

Kuilboer, M. et al., "The Availability of Unavailable Information", AMIA Annual Fall Symp., p. 749-753, 1997.

Leape, L., "Error In Medicine", JAMA, 272, p. 1851-1857, Dec. 21, 1994.

Leape, L. et al., "Promoting Patient Safety By Preventing Medical Error", JAMA, 280, p. 1444-1447, Oct. 28, 1998.

Luxenberg, S. et al., "Electronic Forms: Benefits and Drawbacks of A World Wide Web-Based Approach to Data Entry", Proc. AMIA Annual Fall Symp., p. 804-808, 1997.

Mandl, K. et al., "Electronic Patient-Physician Communication: Problems and Promise", Ann. Intern. Med., 129, p. 495-500, Sep. 15, 1998.

Masys, D. et al., "Patient-Centered Access to Secure Systems Online (PCASSO): A Secure Approach to Clinical Data Access Via the World Wide Web", Proc. AMIA Annual Fall Symp., p. 340-343, 1997.

Auston, I. Et al., "Confidentiality of Electronic Health Data: Methods for Protecting Personally Identifiable Information", National Library of Medicine, CBM 95-100, Mar. 1996.

Neame, R., "Smart Cards—The Key to Trustworthy Health Information Systems", BMJ, 314, p. 573-577, Feb. 22, 1997.

Rind, D. et al., "Maintaining the Confidentiality of Medical Records Shared Over the Internet and the World Wide Web", Ann. Intern. Med., 127, p. 138-141, Jul. 15, 1997.

Schoenberg. R. et al., "Internet Based Repository of Medical Records that Retains Patient Confidentiality", BMJ, 321, p. 1199-1203, Nov. 11, 2000.

Slack, W. et al., "The CCC System in Two Teaching Hospitals: A Progress Report", Int. J. Med. Inf., 54, p. 183-196, Sep. 1999.

Stanberry, B., "The Legal and Ethical Aspects of Telemedicine 1: Confidentiality and the Patient's Rights of Access", J. Telemed. Telecare, 3, p. 179-188, 1997.

Toyada, K., "Standardization and Security for the EMR", Int. J. Med. Inf., 48, p. 57-60, Feb. 1998.

Woodward, B., "The Computer-Based Patient Record and Confidentiality", NEJM, 333, p. 1419-1422, Nov. 23, 1995.

Bell Atlantic and EMX Team Up to Provide Doctors Instant Online Access to Medical Data, PR Newswire, Feb. 23, 1999.

* cited by examiner

TEXT GENERATION AND SEARCHING METHOD AND SYSTEM

RELATED APPLICATIONS

The following U.S. patent is hereby incorporated by reference into the subject application as if set forth herein in full: (1) U.S. Pat. No. 6,463,417, entitled "Method of Distributing Health Information".

FIELD OF THE INVENTION

This invention relates to database record searching, and, more particularly, to text-based searching of database records.

BACKGROUND

The efficient management of large sets of computer-based data is a difficult task. In addition to the physical hardware requirements needed to effectuate the storage of the data, once the data is stored, the management and organization of the data may prove daunting.

Databases are often used to manage and maintain large sets of data, such that the data is organized around a defined database structure. When retrieving data stored within the database, the individual records of the database must be searched. Unfortunately, as the number of records within the database increases, the search time associated with retrieving the data increases dramatically, which often results in unacceptable delay times and latency.

SUMMARY OF THE INVENTION

According to a first implementation, a text-generation method includes receiving data records, such that each data record includes one or more data fields and a field value associated with each data field. A text-string is generated for each data record, such that each text-string includes one or more text-based data descriptors. Each data descriptor includes a field descriptor that defines a specific data field within the data record to which the text-string is related, and a value descriptor that defines the field value associated with the specific data field.

One or more of the following features may also be included. The text-strings may be stored as a text-based data file, such as an ASCII file. Each text-string may include a record identifier that identifies the data record to which the text-string is related. Each data descriptor may include one or more starting characters, one or more separator characters, and one or more ending characters. The field descriptor may be positioned between the separator characters and one of the starting characters and the ending characters. The value descriptor may be positioned between the separator characters and the other of the starting characters and the ending characters. The data records may be representative of the medical records of patients.

According to a further implementation, a search method includes defining a first target value for each of one or more data fields within a database record structure of a database. The database includes a plurality of data records. A plurality of text-strings are searched, such that each text string is associated with one of the data records and includes one or more text-based data descriptors.

Each data descriptor includes a field descriptor that defines a specific data field within the data record to which the text-string is related, and a value descriptor that defines the field value associated with the specific data field.

A first result set is generated by identifying one or more text-strings that include a value descriptor that is essentially equivalent to at least one of the first target values.

One or more of the following features may also be included. The first target values may include one or more wildcard descriptors. The data record associated with one or more of the text-strings identified in the first result set may be retrieved.

A second target value may be defined for each of one or more data fields within the database record structure of the database. The plurality of data records included in the database may be searched, and a second result set may be generated by identifying one or more data records that include a field value that is essentially equivalent to at least one of the second target values. One or more of the data records identified in the second result set may be retrieved.

According to a further implementation, a computer program product resides on a computer readable medium on which a plurality of instructions are stored. When executed by the processor, the instructions cause that processor to: receive data records, such that each data record includes one or more data fields and a field value associated with each data field; and generate a text-string for each data record, such that each text-string includes one or more text-based data descriptors. Each data descriptor includes: a field descriptor that defines a specific data field within the data record to which the text-string is related, and a value descriptor that defines the field value associated with the specific data field.

According to a further implementation, a computer program product resides on a computer readable medium on which a plurality of instructions are stored. When executed by the processor, the instructions cause that processor to: define a first target value for each of one or more data fields within a database record structure of a database, such that the database includes a plurality of data records; search a plurality of text-strings, wherein each text string is associated with one of the data records and includes one or more text-based data descriptors. Each data descriptor includes: a field descriptor that defines a specific data field within the data record to which the text-string is related, and a value descriptor that defines the field value associated with the specific data field. A first result set is generated by identifying one or more text-strings that include a value descriptor that is essentially equivalent to at least one of the first target values.

According to a further implementation, a searching system includes a server system having a computer processor and associated memory, the server system including a database that includes a plurality of data records. The server system is configured to: define a first target value for each of one or more data fields within a database record structure of the database and search a plurality of text-strings. Each text string is associated with one of the data records and includes one or more text-based data descriptors, such that each data descriptor includes: a field descriptor that defines a specific data field within the data record to which the text-string is related, and a value descriptor that defines the field value associated with the specific data field. A first result set is generated by identifying one or more text-strings that include a value descriptor that is essentially equivalent to at least one of the first target values.

According to a further implementation, a data structure includes a database having a plurality of data records, such that each data record includes one or more data fields, and a field value is associated with each data field. The data structure includes a text-string for one or more data records, such that each text-string includes one or more text-based data descriptors. Each data descriptor includes: a field descriptor that defines a specific data field within the data record to which the text-string is related, and a value descriptor that defines the field value associated with the specific data field.

The details of one or more implementations is set forth in the accompanying drawings and the description below. Other features and advantages will become apparent from the description, the drawings, and the claims.

DETAILED DESCRIPTION OF THE PREFERRED EMBODIMENTS

Figure 1:
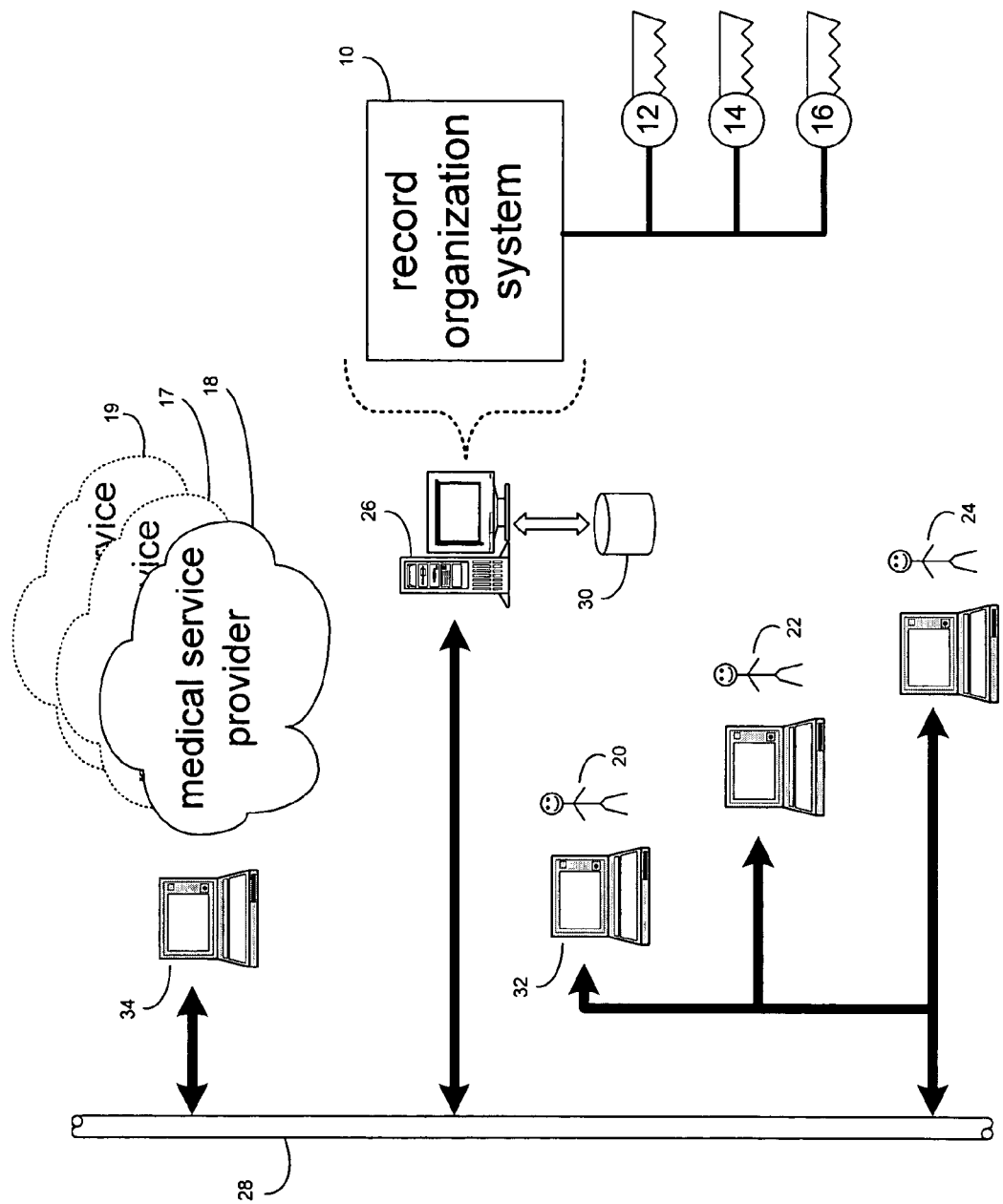
FIG. 1 is a diagrammatic view of a record organization system coupled to a distributed computing network.

Referring to FIG. 1, there is shown a record organization system 10 that manages the various access keys 12, 14, 16 possessed by a medical service provider 18. Access keys 12, 14, 16 allow the medical service provider 18 to access the medical records (not shown) of various patients 20, 22, 24 (respectively).

Record organization system 10 typically resides on and is executed by a computer 26 that is connected to a network 28. Computer 26 may be a web server running a network operating system, such as Microsoft Window 2000 Server™, Novell Netware™, or Redhat Linux™. Typically, computer 26 also executes a web server application, such as Microsoft IIS™, Novell Webserver™, or Apache Webserver™, that allows for HTTP (i.e., HyperText Transfer Protocol) access to computer 26 via network 28.

The instruction sets and subroutines of record organization system 10, which are typically stored on a storage device 30 coupled to computer 26, are executed by one or more processors (not shown) and one or more memory architectures (not shown) incorporated into computer 26. Storage device 30 may be, for example, a hard disk drive, a tape drive, an optical drive, a RAID array, a random access memory (RAM), or a read-only memory (ROM).

As will be explained below in greater detail, a patient (e.g., patient 20) typically provides a key (e.g., access key 12) to medical service provider 18 through a patient computer 32, which is also connected to network 28. Additionally, medical service provider 18 accesses record organization system 10 through a client computer 34.

Figure 2:
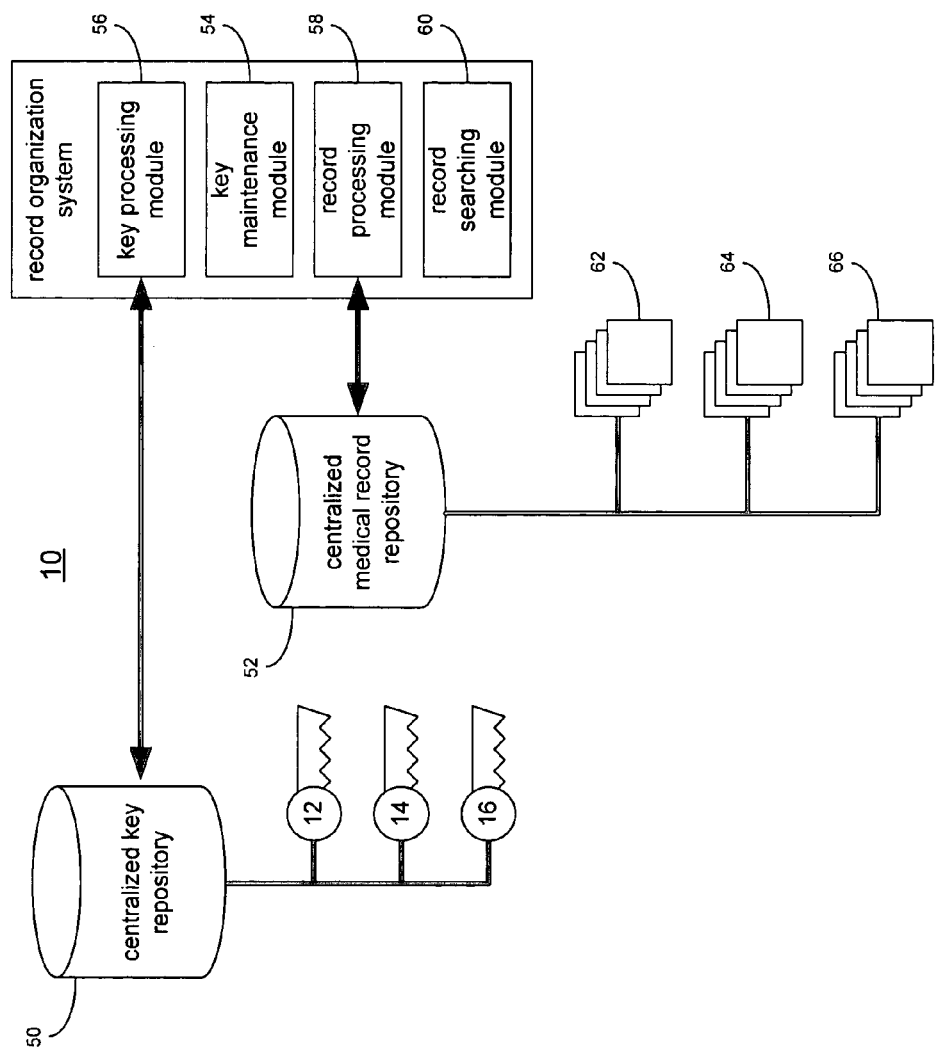
FIG. 2 is a more-detailed diagrammatic view of the record organization system of FIG. 1.

Referring also to FIG. 2, record organization system 10 includes a centralized key repository 50 and a centralized medical records repository 52. Additionally, record organization system 10 includes a key maintenance module 54, a key processing module 56, a record processing module 58, and a record searching module 60, each of which will be discussed below in greater detail.

Centralized medical records repository 52 allows for the centralized storage of medical records 62, 64, 66 concerning various patients 20, 22, 24 respectively. As disclosed in U.S. Pat. No. 6,463,417, medical records 62, 64, 66 are typically divided into portions or levels, in that certain portions are considered more confidential than other portions. For example, a portion/level of the medical record that may be considered the least confidential might include general patient identification information and information concerning the patient's blood type and allergies. A portion/level of a medical record that may be considered to have an intermediate level of confidentiality might include information concerning the serological data, psychiatric data, cardiology data, and genetic data. A portion/level of the medical record that may be considered highly confidential may include infectious disease (e.g., HIV, and sexually transmitted diseases) data.

This specific assignment of confidentiality levels and the apportionment of the medical record into various portions/levels is for illustrative purposes only and is not intended to limit the scope of this disclosure.

Medical records 62, 64, 66 may be incrementally generated/configured online by the various medical service providers that provide care to patients 20, 22, 24. Alternatively, existing medical records may be uploaded (i.e., transferred) to medical records repository 52 from a remote storage location (not shown).

Figure 3:
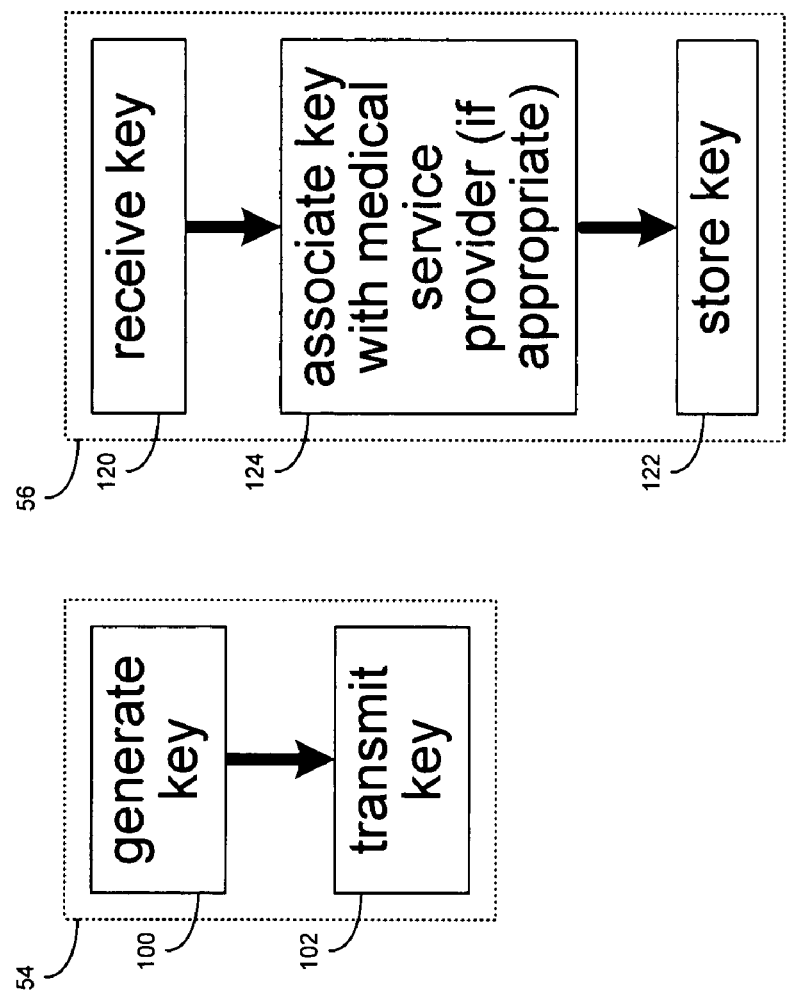
FIG. 3 is a diagrammatic view of a key maintenance module and a key processing module of the record organization system of FIG. 1.

Referring also to FIG. 3, patients 20, 22, 24 use key maintenance module 54 to generate 100 access keys 12, 14, 16 that grant access to various portions of the respective medical records 62, 64, 66. Accordingly, though the use of key maintenance module 54, the patient can generate access keys that not only regulate who has access to their medical records, but also regulate the level of access (i.e., which portions of a patient's medical record are viewable by the medical service provider to which the key is provided). Examples of access keys 12, 14, 16 are passwords (that allow access to various portions of a medical record) and decryption keys (that decrypt various portions of an encrypted medical record).

Typically, key maintenance module 54 is a web-enabled application that is accessed by the patients (e.g., patient 20) through a browser application (e.g., Microsoft Internet Explorer™, or Netscape Navigator™) that is running on patient computer 32. Alternatively, key maintenance module 54 may be a local application that is executed locally on patient computer 32.

As stated above, key maintenance module 54 allows a patient to generate 100 an access key for a specific medical service provider that grants, to that medical service provider, a defined level of access to that patient's medical records. Once this access key is generated, the access key is transmitted 102 to the medical service provider 18. This transmission of the access key may be implemented by transferring the access key from the patient to the medical service provider. This may occur by attaching the access key to an email that is transmitted to the medical service provider. Once received, the medical service provider may then transfer the newly-generated key to the key processing module 56 (to be discussed below in greater detail) of the record organization system 10. Alternatively, the patient may directly transfer the newly-generated key to the key processing module 54 of the record organization system 10.

Regardless of the manner in which the patient transfers the access key to the medical service provider, the access key will ultimately be received 120 by key processing module 56, which receives any access keys (e.g., keys 12, 14, 16) generated and transmitted by patients 20, 22, 24. Once these keys are received 120, they are stored 122 on centralized key repository 50. Additionally, if record organization system 10 is servicing multiple medical service providers (e.g., medical service providers 17, 18, 19), the received keys are associated 124 with the appropriate medical service provider so that the keys transmitted to a first provider are not available to a second provider.

Figure 4:
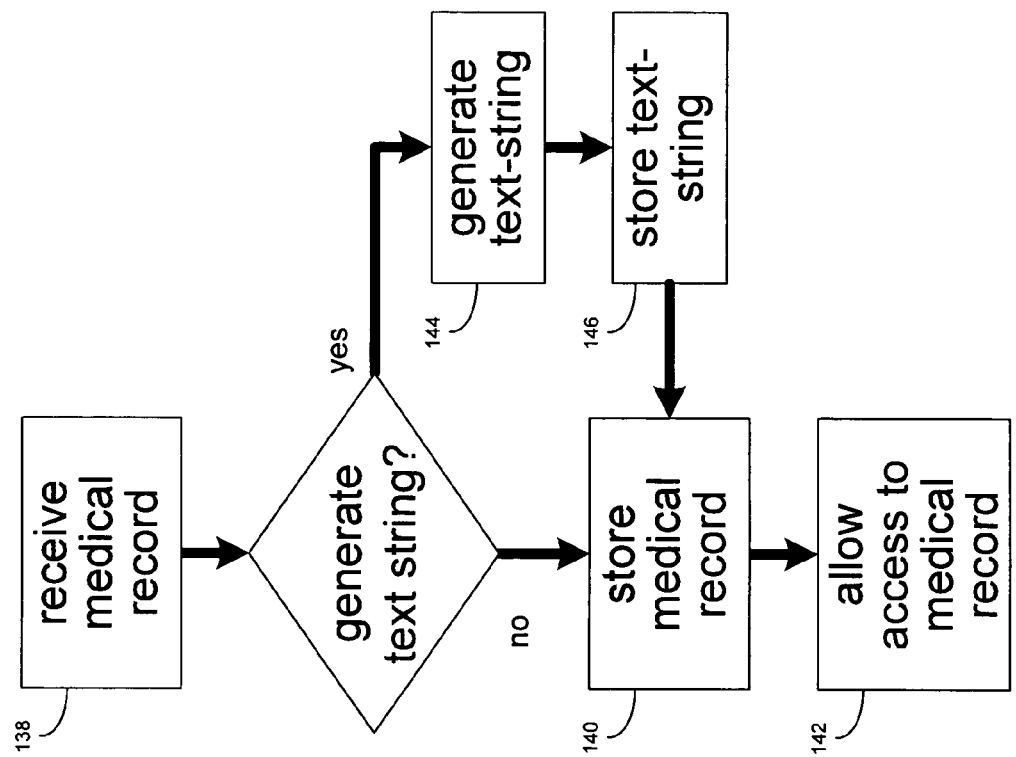
FIG. 4 is a diagrammatic view of a record processing module of the record organization system of FIG. 1.

Referring also to FIG. 4, when medical records (i.e., uploaded existing records, newly-generated records, and/or amended records) are initially received 138, record processing module 58 stores 140 the medical record on centralized medical record repository 52. Typically, medical record repository 52 is a database that allows for the organized storage and retrieval of the medical records 62, 64, 66.

Once these medical records are stored on medical record repository 52, record processing module 58 allows the medical service provider 18 to access 142 the medical records 62, 64, 66 stored on medical records repository 52. However, the medical service provider 18 is only given access to the portions of the medical records for which the medical service provider 18 possesses the appropriate key. For example, assume that medical service provider 18 is a medical clinic that provides an array of medical services to its patients. Further, assume that patient 20 uses medical service provider 18 for all of their medical needs; patient 22 uses medical service provider 18 solely for treatment of depression; and patient 24 uses medical service provider 18 solely for treatment of HIV.

Concerning the access keys generated by each of these patients for medical service provider 18: patient 20 would typically provide medical service provider 18 with an access key (i.e., key 12) that grants access to their entire medical record; patient 22 would typically provide medical service provider 18 with an access key (i.e., key 14) that grants access to the general and psychiatric portions of their medical record; and patient 22 would typically provide medical service provider 18 with an access key (i.e., key 16) that grants access to the general and infectious disease portions of their medical record.

Record processing module 58 is typically a web-enabled application that is accessed by the medical service provider 18 through a browser application (e.g., Microsoft Internet Explorer™, or Netscape Navigator™) that is running on client computer 34. Typically, medical service provider 18 logs into key organization system 10 using an encrypted SSL (i.e., secure sockets layer) connection.

Figure 5:
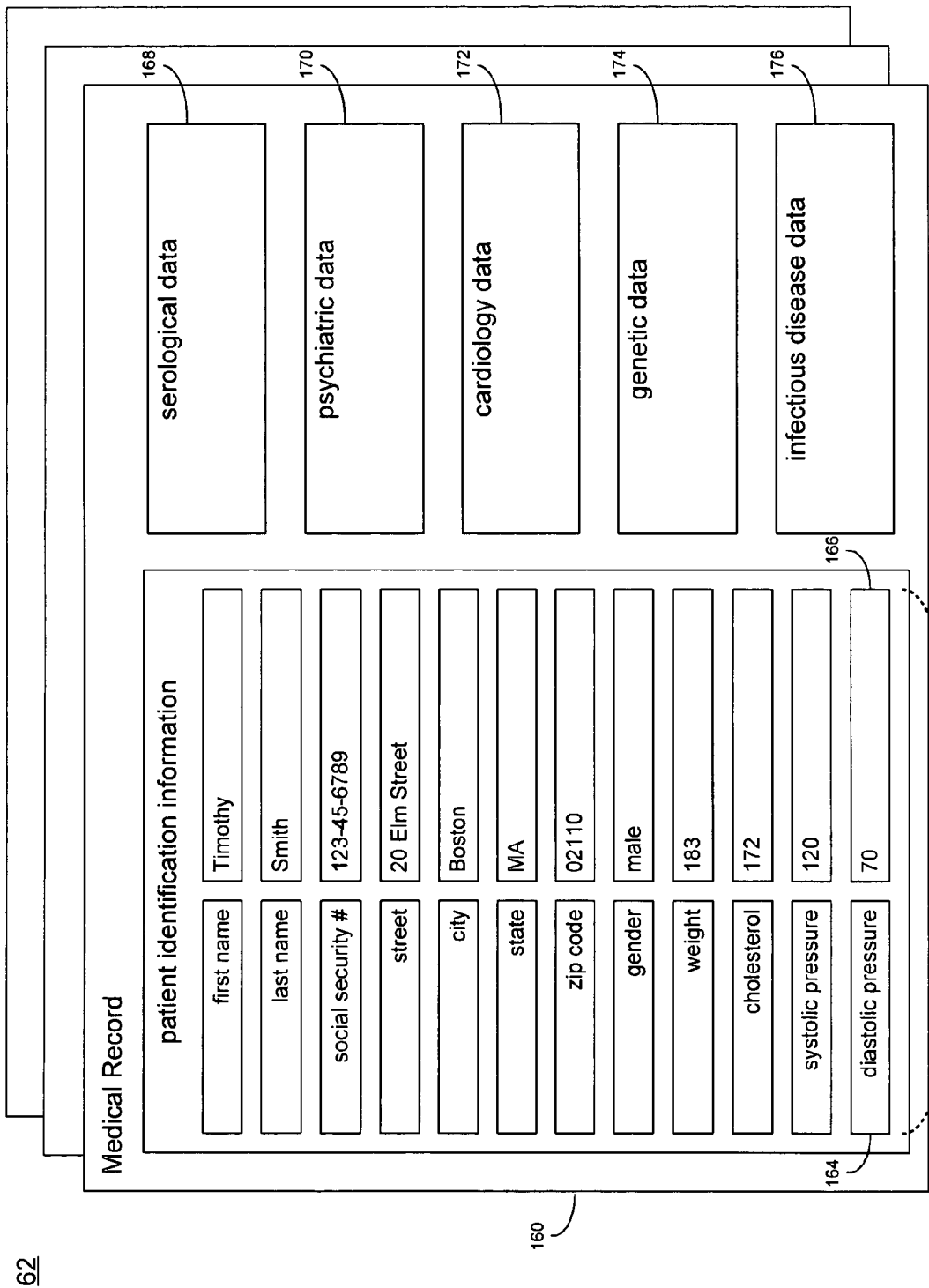
FIG. 5 is a diagrammatic view of a medical record.

Referring also to FIG. 5, medical records 62, 64, 66 are typically database records 160 that contain data fields (e.g., data field 162), each of which includes a field name 164 and a field value 166. Additionally, as discussed above, medical records 62, 64, 66 includes serological data 168, psychiatric data 170, cardiology data 172, genetic data 174, and infectious disease data 176, each of which may be further broken down into data fields.

To enhance the searchability of centralized medical record repository 52, record processing module 58 may process each record to generate 144 a text string that relates to that record. A example of a text string for record 160 is:

<first_name:timothy> <last_name:smith> <ss#: 123456789> <street:20 elm street> <city:boston> <state:ma> <zip:02110> <gender:male> <weight:183> <cholesterol:172> <sys_press:12)> <dia_press:70> <data_record:1243562>

The above-listed text string is a textual representation of the field-based data included within the "patient identification portion" of the medical record 62 of patient 22 (i.e., Timothy Smith).

The text string includes one or more data descriptors (e.g., <dia_press:70>), each of which includes a field descriptor (e.g., dia_press) and a field value (e.g., 70). The field descriptor and the field value are typically separated by a separator character (e.g.,:), and the data descriptor begins with beginning characters (e.g., <) and ends with ending characters (e.g., >).

The field descriptor defines a specific data field within the data record to which the text-string is related. For example, the field descriptor "dia_press" relates to data field 164 in record 62. Further, the value descriptor defines the field value associated with the same specific data field. For example, the value descriptor "70" relates to field value 166

The text string typically also includes a record identifier (e.g., <data_record:1243562>) that associates the text-string with the medical record upon which the text-string is based, so that the medical record may be subsequently retrieved.

The text-strings generated by record processing module 58 are typically stored 146 within centralized medical record repository 52. The text-strings may be stored in a group as a single text file, such as an ASCII (i.e., American Standard Code for Information Interchange) file. Alternatively, the text-strings may be stored as individual text-based files. Regardless of the manner in which the text-strings are stored, as will be discussed below, by searching the text strings for the occurrence of specific data descriptors, the medical records that contain desired information may be quickly identified.

Figure 6:
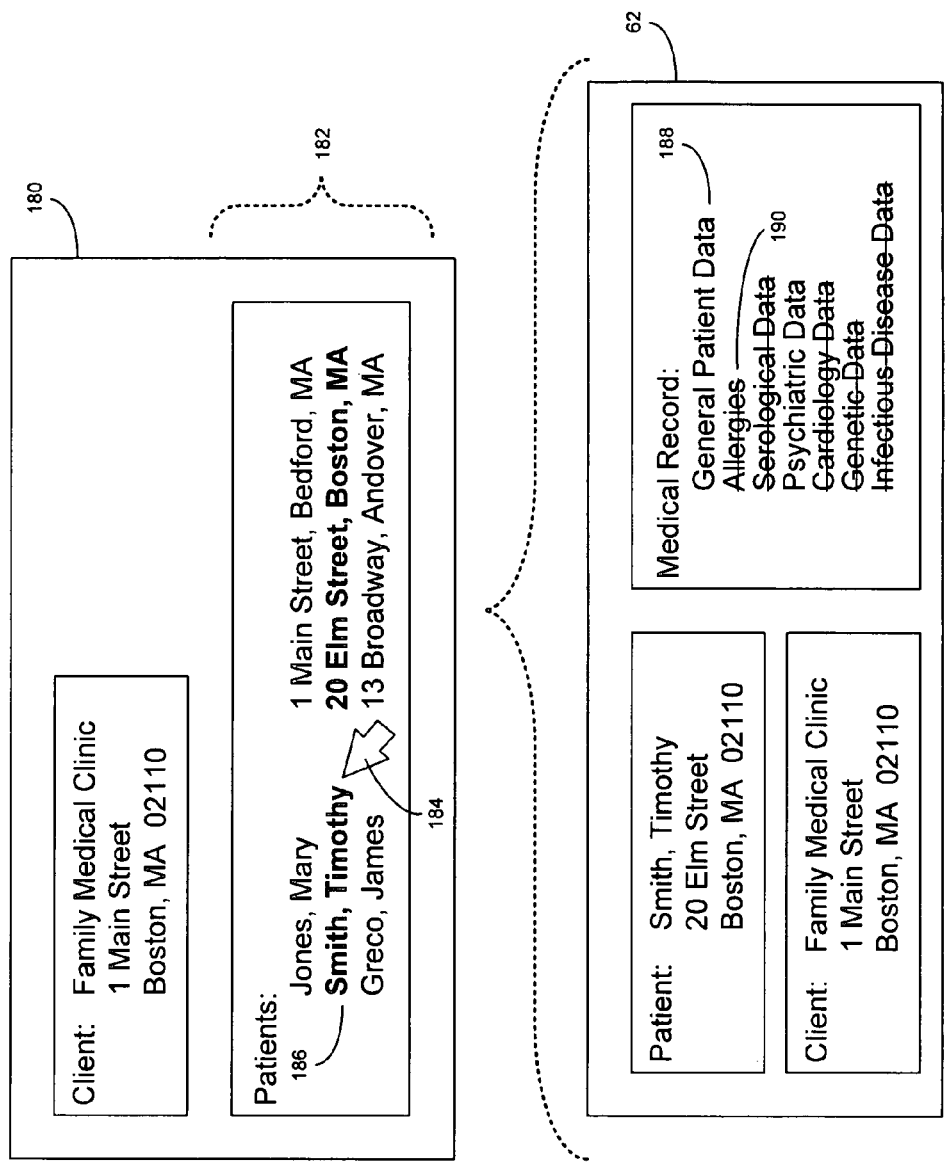
FIG. 6 is a diagrammatic view of a patient selection display screen rendered by the record organization system of FIG. 1.

Referring also to FIG. 6, when accessing record organization system 10, record processing module 58 provides the medical service provider 18 with a rendered screen display 180 that includes a list of patient identifiers 182. Patient identifiers 182 define the particular patient(s) who provided access keys to medical service provider 18 (i.e., granting medical service provider 18 access to various portions of their medical record(s)). The patient identifiers 182 may be any element that uniquely identifies the patient, such as the patient's name, the patient's social security number, or a unique patient number. In this particular example, Mary Jones is patient 20, Timothy Smith is patient 22, and James Greco is patient 24.

The presence of each of these names in the list of patient identifiers 182 indicates that a key was received from that patient. In order to access the medical record of a patient for which the medical service provider has a key (i.e., for one of the patients listed in the list of patient identifiers 182), the medical service provider 18 selects the appropriate identifier using a mouse pointer 184 (or some other pointing device, not shown). For example, if the medical service provider wanted to access the medical record of Timothy Smith (i.e., patient 22), medical service provider 18 would typically click (using a mouse) on the specific identifier 186 associated with Timothy Smith. Record processing module 58 would then, in turn, use access key 14 to access (i.e., retrieve, decrypt, and display) medical record 64, the medical record of Timothy Smith, i.e., patient 22.

Medical record 64 may be displayed in a separate window or displayed full screen on the display of client computer 34. As discussed above, the key provided to the medical service provider 18 only allows access to the portion(s) of the patient's medical record that the patient wishes to allow access. As discussed above, Timothy Smith (i.e., patient 22) is being treated by medical service provider 18 for depression and access key 14 grants access to the general and psychiatric portions of Timothy Smith's medical record, such that a link (e.g., link 188) to each available portion is displayed on the right-hand side of medical record 62. However, access key 14 does not permit access (i.e., prohibits access) to the other portions of Timothy Smith's medical record, namely Allergies, Serological Data, Cardiology Data, Genetic Data, and Infectious Disease Data. Accordingly, the links (e.g., link 190) to the unavailable data portions are struck-through. Other methods of differentiating the available portions from the unavailable portions of a medical record may be used, such as graying-out or not displaying links to the unavailable portions.

By clicking on the links to the available portions of the medical record, a specific available portion is displayed by record processing module 58.

Figure 7:
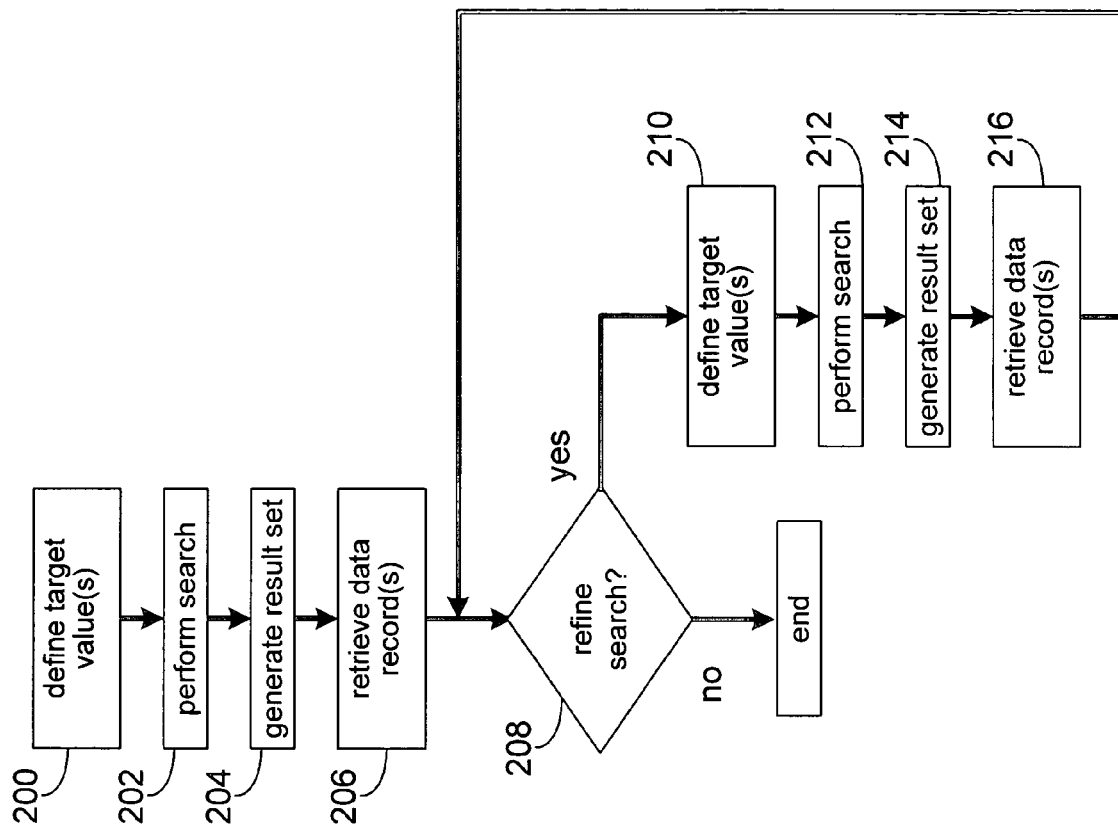
FIG. 7 is a diagrammatic view of a record searching module of the record organization system of FIG. 1.

Referring also to FIG. 7, record searching module 60 facilitates the searching of medical records stored on the centralized medical record repository 52. This searching may be performed by a medical service provider (e.g., medical service provider 18) or an administrator of record organization system 10. However, the party doing the searching may only search the portions of the medical records to which they are granted access. This access may be based on the possession of keys (i.e., for medical service providers) or administrative privileges (i.e., for administrators), for example.

Record searching module 60 allows a user (e.g., a medical service provider, an administrator, etc.) to define 200 a target value for one or more of the data fields (e.g., data field 162) within the database record structure of the medical records (e.g., medical record 62) stored on centralized medical record repository 52. The database record structure refers to the field structure of a database records. For example, database record 62 includes twelve specific data fields (namely, first name, last name, social security number, street, city, state, zip code, gender, weight, cholesterol, systolic pressure, and diastolic pressure) and five data portions (namely serological data, psychiatric data, cardiology data, genetic data, and infectious disease data). As stated above, the patient controls the access to the various portions of their medical record through the use of access keys. Additionally, these portions are typically subdivided into numerous data fields.

Typically, record searching module 60 is a web-enabled application that is accessed by the user (e.g., medical service provider 18) through a browser application (e.g., Microsoft Internet Explorer™, or Netscape Navigator™) that is running on a computer (e.g., client computer 34). Alternatively, record searching module 60 may be a locally-executed application.

Figure 8:
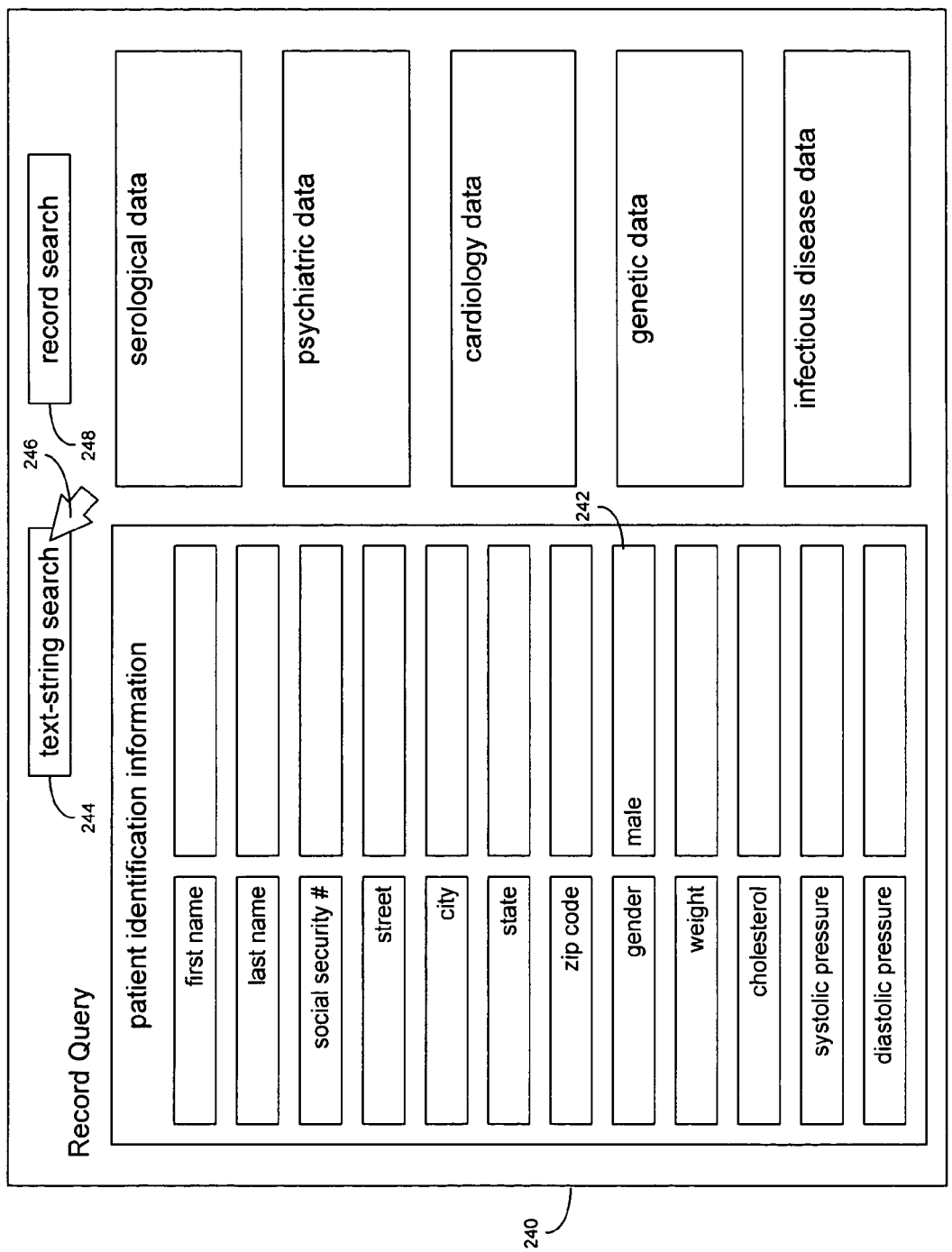
FIG. 8 is a diagrammatic view of a query definition display screen rendered by the record organization system of FIG. 1.

Referring also to FIG. 8, when a user initiates a search, a query definition display 240 is rendered by record searching module 60 that allows the user to define 200 the search terms (i.e, target values) of a database record query. For example, if medical service provider 18 wished to search the medical records (to which they have access) to determine which of their patients were male, medical service provider 18 would enter the search term "male" into field 242 of display 240. These search terms may be whole words, portions of words, and/or wildcard descriptors (e.g., *).

Medical service provider 18 would then initiate 202 the search by "clicking" on the text-string search button 244 with mouse pointer 246. As, in the example, medical service provider 18 only has access to the medical records of three patients, namely Mary Jones (i.e., patient 20), Timothy Smith (i.e., patient 22), and James Greco (i.e., patient 24), the result list (not shown) for the query would include two entries, namely Timothy Smith and James Greco.

When executing a text-string based search, the search is executed by associating the search term(s) entered (i.e., "male") with the data field into which that search term was entered (i.e., "gender"). This, in turn, generates a search term in the form of a data descriptor (i.e., <gender:male>). Therefore, when executing the text-string search, the text string for each medical record available to the initiator of the search is examined to determine if any of these text strings contain the search term data descriptor. As discussed above, the text-string associated with patients Timothy Smith (i.e., patient 22) and James Greco (i.e., patient 24) include the data descriptor <gender:male>. Additionally, each text-string includes a record identifier that associates the text-string to the medical record on which it is based. Therefore, once the relevant text strings are determined, the related medical records are easily ascertained. By performing text-based searches on text-strings, the search speed is increased and latency is reduced.

The result list (not shown) generated 204 in response to this query includes the names of Timothy Smith and James Greco. Typically, the result list is in the form of an HTML document. As the patient names are typically embedded links, when the user clicks on one or more of these links, the corresponding medical record is retrieved 206.

In addition to the text-based searches performed above, a record-based search may also be performed. Typically, a text-based search is performed as an initial search to generate a first result set. Often, this result set is quite large and, therefore, a secondary search may be performed on the first result set. Accordingly, once a determination 208 is made that the first result set needs to be further reduced in size, a secondary record-based search may be performed by defining 210 additional search terms (i.e., target values) that further restrict the result set. The new search is then performed 212 and a refined result set is generated 214 and presented to the user.

Assuming that James Greco weighs 230 pounds, if the additional search term defines the desired weight as "<200 pound", Timothy Smith will be the only patient specified in the second result set, as he weighs 183 pounds. As above, the medical record(s) specified in the second result set are easily retrieved 216 by clicking on the appropriate link. The search terms may be repeatedly refined until the result set is reduced to a size acceptable to the user.

As stated above, the secondary query may be performed using traditional record-based searching technique employed by database search engines. If record-based searching is desired, a record based search is initiated 212 by "clicking" on the record-based search button 248 with mouse pointer 246.

While medical record 66 is shown to include a plurality of links to the available portions of the medical record, other configurations are possible. For example, when clicking on a specific identifier (e.g., identifier 164), a medical record may be displayed that only includes the portions to which the medical service provider has access.

While the centralized key repository 50 and the centralized medical record repository 52 are described above as being located on a remote server, other configurations are possible. For example, as is known in the art, one or more of these repositories may be distributed across multiple computers/servers.

A number of implementations have been described. Nevertheless, it will be understood that various modifications may be made. Accordingly, other implementations are within the scope of the following claims.

What is claimed is:

1. A text-generation method comprising:
    receiving, into a record processing module of a system, data records, wherein each data record includes one or more data fields and a field value associated with each data field; and
    said record processing module generating, for application in efficiently searching for desired ones of said data records, a text-string for each data record, wherein each text-string includes one or more text-based data descriptors, such that each data descriptor includes:
    a field descriptor that defines a specific data field within the data record to which the text-string is related; and
    a value descriptor that defines the field value associated with the specific data field.

2. The text-generation method of claim 1 further comprising storing the text-strings as a text-based data file.

3. The text-generation method of claim 2 wherein the text-based file is an ASCII file.

4. The text-generation method of claim 1 wherein each text-string further includes a record identifier that identifies the data record to which the text-string is related.

5. The text-generation method of claim 1 wherein each data descriptor includes one or more starting characters, one or more separator characters, and one or more ending characters.

6. The text-generation method of claim 5 wherein the field descriptor is positioned between the separator characters and one of the starting characters and ending characters.

7. The text-generation method of claim 6 wherein the value descriptor is positioned between the separator characters and the other of the starting characters and the ending characters.

8. The text-generation method of claim 1 wherein the data records is representative of the medical records of patients.

9. A search method comprising:
    defining a first target value for each of one or more data fields within a database record structure of a database, wherein the database includes a plurality of data records;
    searching a plurality of text-strings, wherein each text string is associated with one of the data records and includes one or more text-based data descriptors, such that each data descriptor includes:
    a field descriptor that defines a specific data field within the data record to which the text-string is related, and
    a value descriptor that defines the field value associated with the specific data field; and
    generating a first result set by identifying one or more text-strings that include a value descriptor that is essentially equivalent to at least one of the first target values.

10. The search method of claim 9 wherein one or more of the first target values includes one or more wildcard descriptors.

11. The search method of claim 9 further comprising retrieving the data record associated with one or more of the text-strings identified in the first result set.

12. The search method of claim 9 wherein the text-strings may be stored as a text-based data file.

13. The search method of claim 12 wherein the text-based data file is an ASCII file.

14. The search method of claim 9 wherein each text-string further includes a record identifier for associating the text-string and the data record to which the text-string is related.

15. The search method of claim 9 wherein each data descriptor includes one or more starting characters, one or more separator characters, and one or more ending characters.

16. The search method of claim 15 wherein the field descriptor is positioned between the separator characters and one of the starting characters and the ending characters.

17. The search method of claim 16 wherein the value descriptor is positioned between the separator characters and the other of the starting characters and the ending characters.

18. The search method of claim 9 further comprising:
    defining a second target value for each of one or more data fields within the database record structure of the database;
    searching the plurality of data records included in the database; and
    generating a second result set by identifying one or more data records that include a field value that is essentially equivalent to at least one of the second target values.

19. The search method of claim 18 further comprising retrieving one or more of the data records identified in the second result set.

20. The search method of claim 9 wherein the data records is representative of the medical records of patients.

21. A computer program product residing on a computer readable medium having a plurality of instructions stored thereon which, when executed by the processor, cause that processor to:
    receive data records, wherein each data record includes one or more data fields and a field value associated with each data field; and
    process the received data records to generate, for application in efficiently searching for desired ones of said data records, a text-string for each data record, wherein each text-string includes one or more text-based data descriptors, such that each data descriptor includes:
    a field descriptor that defines a specific data field within the data record to which the text-string is related, and
    a value descriptor that defines the field value associated with the specific data field.

22. The computer program product of claim 21 further comprising instructions for storing the text-strings as a text-based data file.

23. The computer program product of claim 22 wherein the text-based data file is an ASCII file.

24. The computer program product of claim 21 wherein each text-string further includes a record identifier that identifies the data record to which the text-string is related.

25. The computer program product of claim 21 wherein each data descriptor includes one or more starting characters, one or more separator characters, and one or more ending characters.

26. The computer program product of claim 25 wherein the field descriptor is positioned between the separator characters and one of the starting characters and the ending characters.

27. The computer program product of claim 26 wherein the value descriptor is positioned between the separator characters and the other of the starting characters and the ending characters.

28. The computer program product of claim 21 wherein the data records is representative of the medical records of patients.

29. A computer program product residing on a computer readable medium having a plurality of instructions stored thereon which, when executed by the processor, cause that processor to:
    define a first target value for each of one or more data fields within a database record structure of a database, wherein the database includes a plurality of data records;

search a plurality of text-strings, wherein each text string is associated with one of the data records and includes one or more text-based data descriptors, such that each data descriptor includes:
  a field descriptor that defines a specific data field within the data record to which the text-string is related, and
  a value descriptor that defines the field value associated with the specific data field; and
generating a first result set by identifying one or more text-strings that include a value descriptor that is essentially equivalent to at least one of the first target values.

30. The computer program product of claim 29 wherein one or more of the first target values includes one or more wildcard descriptors.

31. The computer program product of claim 29 further comprising instructions for retrieving the data record associated with one or more of the text-strings identified in the first result set.

32. The computer program product of claim 29 wherein the text-strings may be stored as a text-based data file.

33. The computer program product of claim 32 wherein the text-based data file is an ASCII file.

34. The computer program product of claim 29 wherein each text-string further includes a record identifier for associating the text-string and the data record to which the text-string is related.

35. The computer program product of claim 29 wherein each data descriptor includes one or more starting characters, one or more separator characters, and one or more ending characters.

36. The computer program product of claim 35 wherein the field descriptor is positioned between the separator characters and one of the starting characters and the ending characters.

37. The computer program product of claim 36 wherein the value descriptor is positioned between the separator characters and the other of the starting characters and the ending characters.

38. The computer program product of claim 29 further comprising instructions for:
  defining a second target value for each of one or more data fields within the database record structure of the database;
  searching the plurality of data records included in the database; and
  generating a second result set by identifying one or more data records that include a field value that is essentially equivalent to at least one of the second target values.

39. The computer program product of claim 38 further comprising instructions for retrieving one or more of the data records identified in the second result set.

40. The computer program product of claim 29 wherein the data records is representative of the medical records of patients.

41. A searching system comprising:
  a server system including a computer processor and associated memory, the server system having a database that includes a plurality of data records;
  wherein the server system is configured to:
  define a first target value for each of one or more data fields within a database record structure of the database;
  search a plurality of text-strings, wherein each text string is associated with one of the data records and includes one or more text-based data descriptors, such that each data descriptor includes:
    a field descriptor that defines a specific data field within the data record to which the text-string is related, and
    a value descriptor that defines the field value associated with the specific data field; and
  generate a first result set by identifying one or more text-strings that include a value descriptor that is essentially equivalent to at least one of the first target values.

42. The searching system of claim 41 wherein the server system is further configured for retrieving the data record associated with one or more of the text-strings identified in the first result set.

43. The searching system of claim 41 wherein the server system is further configured for:
  defining a second target value for each of one or more data fields within the database record structure of the database;
  searching the plurality of data records included in the database; and
  generating a second result set by identifying one or more data records that include a field value that is essentially equivalent to at least one of the second target values.

44. The searching system of claim 43 wherein the server system is further configured for retrieving one or more of the data records identified in the second result set.

45. The searching system of claim 41 wherein the data records is representative of the medical records of patients.

46. The searching system of claim 41 wherein the server system is coupled to a distributed computing network.

* * * * *